United States Patent [19] [11] Patent Number: 5,130,325
Smith [45] Date of Patent: Jul. 14, 1992

[54] METHOD FOR CONTROLLING PLANT DISEASE AND MICROORGANISMS BY INCORPORATION OF N-HALOHYDANTOIN INTO NUTRIENT-WATERING SUPPLIES

[75] Inventor: Roger E. Smith, West Lafayette, Ind.

[73] Assignee: Great Lakes Chemical Corporation, West Lafayette, Ind.

[21] Appl. No.: 774,388

[22] Filed: Oct. 11, 1991

Related U.S. Application Data

[63] Continuation of Ser. No. 677,474, Mar. 29, 1991, abandoned, which is a continuation of Ser. No. 316,519, Feb. 28, 1989, abandoned, which is a continuation-in-part of Ser. No. 278,722, Dec. 2, 1988, abandoned, which is a continuation of Ser. No. 925,321, Oct. 31, 1986, abandoned.

[51] Int. Cl.$^5$ .......................................... A61K 31/415
[52] U.S. Cl. ................................ 514/389; 71/3; 71/67
[58] Field of Search .................... 514/389; 71/3, 67

[56] References Cited

U.S. PATENT DOCUMENTS

4,058,618  1/1977  Ovchinnikov et al. ............. 514/389
4,167,832  9/1979  Zetterquist et al. .................. 47/1 R
4,655,815  4/1987  Jakubowski ............................. 71/67

FOREIGN PATENT DOCUMENTS

1472049  4/1975  United Kingdom .

Primary Examiner—John W. Rollins
Attorney, Agent, or Firm—Senniger, Powers, Leavitt & Roedel

[57] ABSTRACT

A method for controlling plant diseases and unwanted microorganisms by incorporating N-halohydantoins in nutrient-watering solutions. In the method, a treatment mixture is prepared comprising plant nutrients, N-halohydantoin and water. A plant is contacted with the treatment mixture to inhibit disease or the growth of unwanted microorganisms on, in or around the plant, with the mixture also being viable for use in stimulating healthy plant growth.

22 Claims, No Drawings

METHOD FOR CONTROLLING PLANT DISEASE AND MICROORGANISMS BY INCORPORATION OF N-HALOHYDANTOIN INTO NUTRIENT-WATERING SUPPLIES

This is a continuation of application Ser. No. 667,474 filed ON Mar. 29, 1991, now abandoned, which is a continuation application of Ser. No. 316,519, filed Feb. 28, 1989, now abandoned, which is a continuation-in-part of Ser. No. 07/278,722, filed Dec. 2, 1988, which is a continuation of Ser. No. 925,321, filed Oct. 31, 1986, both now abandoned.

This invention relates to plant diseases and deleterious microorganisms found in environments adapted for the growth of higher order plants, and more particularly, to control and inhibition of plant diseases and deleterious microorganisms found in such environments by incorporation of N-halohydantoin in nutrient-watering supplies.

An effective irrigation system is an important feature of many greenhouses, outdoor nurseries, crop fields and other environments adapted for the growth of higher order plants. In addition to Providing a source of water for the plants, irrigation systems have commonly been designed to provide for the incorporation and delivery of nutrients required by the plants for healthy growth and development.

A wide array of irrigation systems are in use today as a result of the great diversity of agricultural production systems and the differing watering requirements of various plants. Examples of these systems include sprinkler, trickle, mist, sub-irrigation, ebb-and-flow, and hydroponic irrigation. A sprinkler system operates by use of sprinklers or nozzles spraying water over the crop. Trickle, or drip, irrigation employs delivery systems in which tubes perforated with tiny holes or emitters are calibrated to provide precisely measured amounts of water to the crop. Mist, or fog, systems, employed most commonly in enclosed propagation areas such as greenhouses, use special nozzles to generate mists which irrigate the plants and cool the greenhouse. Sub-irrigation is employed by delivering water to the plants by means of a mat placed underneath pots containing the plants. The mat is saturated intermittently with water to allow the plant to absorb water as needed through the bottom of the pot. In ebb-and-flow irrigation, water is applied to plants through channels between rows of pots on benches, generally several times each day and allowed to drain between cycles. Hydroponic irrigation systems involve the growth of plants in soil-less cultures containing a nutrient water solution.

The efficiency and labor saving design of modern irrigation systems has also led to the wide-spread utilization of irrigation water to deliver essential nutrients to crops and other plants. Nitrogen, potassium, phosphorus and other nutrients are readily dissolved in irrigation water and thereby carried to the plants as the plants are being irrigated. While such nutrient-watering systems are very beneficial, they are not without problems, particularly relating to the growth of such deleterious microorganisms as algae, slime and pathogenic bacteria. Plant disease causing organisms my sometimes be found in contaminated sources of irrigation water, or be introduced by other sources such as new plants brought into the greenhouse or nursery, and then transmitted through the water supply to plants serviced by the irrigation system. Indeed, the typical greenhouse or outdoor nursery is an ideal breeding ground for algal, fungal, bacterial and viral organisms, having ample quantities of fertilizer, water and light to foster their growth.

Pathogenic diseases and deleterious microorganisms can seriously undermine the economic viability of horticulture operations, virtually wiping out whole stocks of plants if not checked. This is particularly a problem where recirculating irrigation systems are employed since the recirculating water can serve as a vehicle to transport carriers of the disease from sick to healthy plants. Contaminated surface water may also pose a plant health problem. Development of bacteria, fungus and algae causes spoiling of plants and their fruits, and otherwise harms higher order plants. Development of pathogenic microorganisms such as Verticillium, Pythium, Fusarium, Alternaria and Xanthomonas in or on plants also causes various plant diseases.

Additionally, microorganisms prevalent in environments adapted for growing plants, in contaminated water supplies, etc., greatly undermine the efficiency of the water irrigation system itself by plugging, biofouling and contaminating the water distribution equipment. Growth of slime bacteria, for instance, has the propensity to foul the system and clog irrigation equipment, thereby reducing its efficiency.

Previous attempts to inhibit microorganism development in plant environments either have failed or have been self-defeating because ordinary biocides or disinfectants, such as bleach or various quaternary ammonium compounds, that have been employed to kill or inhibit microorganisms, also are toxic to the higher order plants. This phytotoxicity results from either the direct effect of these biocides, or from the activity of fumes and residues associated with their use. For example, phytotoxic residues, such as copper sulfate, may build up in the growth medium of the greenhouse or nursery. Because such biocides are phytotoxic, they cannot be considered for direct plant treatment. Other biocides, while not significantly phytotoxic, have been associated with health hazards to humans that handle, store or apply the biocides or eat the treated plants or their edible portions.

Another significant obstacle to the use of biocides to control the growth of plant diseases and microorganisms in environments adapted to growing plants has been the expectation that concurrent application of an oxidizing biocide, particularly a halogen-releasing biocide, and fertilizer to plants would interfere with the function of the biocide or of the nutrients, or of both. Incompatibility of such a biocide with plant nutrients would not only severely inhibit the usefulness of the biocide for direct application to growing plants, but would also practically eliminate the use of the biocide for maintaining irrigation mats, equipment and sprinklers free from slime bacteria, algae and other microorganisms. The intimate contact of these systems with nutrient-containing irrigation water would prohibit utilization of such a biocide.

The oxidizing biocides used in the prior art for treating microorganism development around plants typically involve other significant disadvantages. Some are associated with environmental health hazards. These hazards may result from toxic spills of chlorine gas tanks, for example, or from the formation of chloramines, which produce residual compounds which undesirably persist in the environment, when chlorine-releasing biocides come into the presence of ammonia.

Additionally, many of the biocides previously available are unstable in the presence of organic matter, or are effective in only a narrow pH range. Also difficulties in administering biocides, such as prevention of toxic overdoses due to high water solubility, and the cost of expensive equipment for regulating the concentration of additives, have posed additional dilemmas for efforts to control plant diseases and problem microorganisms.

As disclosed in Paterson, U.S. Pat. No. 3,412,021 and Macchiarolo U.S. Pat. No. 4,297,224, 1-bromo-3-chloro-5,5-dimethylhydantoin is known as an oxidizing biocide for use in water treatment in certain environments in which higher order plants are not a concern. Patent and other technical literature discloses a number of uses for this and other N-halohydantoin compounds based on the biocidal properties of these compounds.

SUMMARY OF THE INVENTION

Among the several objects of the invention, therefore, may be noted the provision of a method for controlling unwanted microorganisms located on, in or near growing higher order plants which is not harmful to such plants; provision of such a method that also provides a supply of nutrients to the plants provision of a method that inhibits the spread of plant disease and unwanted microorganisms by water contaminated with such microorganisms; provision of a method for control of unwanted microorganisms which impede the efficiency of the water irrigation system and foul and clog irrigation equipment; provision of a method which simplifies the logistics and reduces the cost of fertilizing of plants and controlling plant disease and growth of unwanted microorganisms; and the provision of a method for irrigating plants whereby development of unwanted microorganisms are inhibited and nutrients are supplied.

Briefly, therefore, the present invention is directed to a novel method for controlling the growth of disease and microorganisms in, on or around higher order plants by addition of N-halohydantoin to nutrient-watering supplies without adversely affecting the growth of higher order plants, or impairing their uptake or utilization of nutrients. The method comprises preparing a treatment mixture comprising plant nutrients, an N-halohydantoin and water, and contacting a plant with said treatment mixture, thereby inhibiting the growth of disease or unwanted microorganisms on, in or around said plant, said treatment mixture being viable for use in stimulating healthy plant growth.

The present invention is also drawn to a novel method for irrigating growing plants wherein needed nutrients are supplied to the plants and growth of disease and unwanted microorganisms is inhibited without harming the higher order plants. The method comprises preparing treated water containing plant nutrients and an N-halohydantoin and continuously or recurrently irrigating plants with the treated water. Alternatively, the method comprises arranging plants and a water-absorbent material so that water may be transported through the water-absorbent material to contact the plants or a growth medium in which they are rooted, preparing treated water containing plant nutrients and an N-halohydantoin and continuously or recurrently delivering the treated water to the water-absorbent material, thereby effecting transport of treated water to the plants or their growth medium.

The present invention is further directed to a novel method for controlling disease or growth of unwanted microorganisms in a growing plant or its rhizosphere without harming the plant while supplying needed nutrients to the plant. The method comprises applying an N-halohydantoin to a growth medium in which the plant is rooted, the N-halohydantoin being continuously or recurrently dissolved in and conveyed to the plant's rhizosphere by irrigated water received by the growth medium in which nutrients have been incorporated.

The present method is also drawn to a novel method for controlling disease or growth of unwanted microorganism in, on or around higher order plants without harming the higher order plant. The method comprises incorporating an N-halohydantoin in water to produce treated water and contacting a plant with the treated water, thereby inhibiting the growth of disease or unwanted microorganisms on, in or around the plant.

The present method is further directed to a novel method for controlling disease or growth of unwanted microorganisms in a hydroponic cultivation system without harming the growth of plants therein. The method comprises preparing treated water containing plant nutrients and an N-halohydantoin and continuously or recurrently irrigating plants in the hydroponic cultivation system with the treated water.

DESCRIPTION OF THE PREFERRED EMBODIMENT

In accordance with the present invention, it has been discovered that N-halohydantoins, their metabolites and residuals, can be used for effective control of microorganisms in a plant environment without risk of injury to higher order plants. The method further provides for supply of nutrients to the plant and comprises a more efficient and simplified scheme for providing both plant fertilization and protection of growing plants from plant diseases and other unwanted microorganisms.

Importantly, it has been discovered that, contrary to what would reasonably have been expected by those skilled in the art, N-halohydantoins may be incorporated, at effective levels, directly into the watering supply containing nutrients for growing plants without adversely affecting the performance of either the N-halohydantoins or the nutrients. Because N-halohydantoin is an oxidizing biocide which derives its effectiveness from its halogen-releasing quality, there were reasons to anticipate that using N-halohydantoin compositions together with fertilizer would result in an unstable mixture that adversely affected the performance of the biocide or interfered in the uptake of essential nutrients by growing plants. Instead, N-halohydantoin has been demonstrated by this invention to be compatible with fertilizers in the same solution at practical levels, and thus may be freely incorporated into nutrient-containing watering supplies, avoiding the necessity of establishing two completely separate systems for the direct delivery of nutrients and biocide to growing plants. It also permits disinfection or microorganism control in irrigation equipment and other systems which come into contact with irrigation water by the incorporation of N-halohydantoin in the nutrient watering supply.

While we do not wish to be bound to a particular theory, it appears that the effectiveness of this process comes from the favorable coincidence of several factors: 1) N-halohydantoin is effective at low levels to control plant pathogens, 2) N-halohydantoin at such levels does not harm growing higher order plants and does not impair the uptake of essential nutrients, 3) N-halohydantoin at such low levels is not extinguished by reaction with nutrients and, 4) N-halohydantoin concentrations in water supplies is self-regulating at safe and effective levels because of its low solubility in water. As a result, it has been found that aqueous solutions of N-halohydantoins may be formulated in a wide, easily attainable range of concentrations that are high enough to kill various unwanted microorganisms such as slime bacteria, viruses, fungus and algae, yet low enough not to harm higher order plants or to interfere with the uptake or utilization of nutrients also incorporated in the water. Regulation of the concentration of N-halohydantoin is simplified by the relatively low solubility of these compounds in water, and the fact that the highest concentration of N-halohydantoin that is obtained under ordinary conditions is too low to result in phytotoxicity or interference with nutrient uptake. It has further been found that solid state N-halohydantoins are not harmful to higher order plants, and that these biocides may thus be applied in either solid or solution form in plant environments, or indeed to the plants themselves, without risk of injury to plant systems or tissue.

Moreover, use of N-halohydantoin by incorporation in nutrient-watering supplies results in many additional advantages. Since ingestion of reasonable amounts of N-halohydantoins is not believed to pose health dangers to humans from toxicity, ingestion of plants or parts thereof treated with N-halohydantoin is believed to present no serious or appreciable health risk. Nor does incidental contact in the handling or application of N-halohydantoin pose a serious health risk. Further, since N-halohydantoins are not flammable under normal circumstances, nor typically stored in pressurized containers, they do not present significant dangers from explosions. The N-halohydantoins of this invention also show greater stability in the presence of organic matter and effectiveness over a wider pH range than shown by typical chlorine disinfectants of the prior art. Additionally, the N-halohydantoins of this invention do not tend to form chloramines in the presence of ammonia, and so are not believed to form residual compounds which undesirably persist and remain in the environment.

According to the method of the invention, N-halohydantoins may be incorporated directly into irrigation water to control the growth of microorganisms in or on the plants irrigated, in the water, on the irrigation equipment and on surfaces contacted by the water. Thus, the transmission of pathogenic microorganisms through the irrigation network can be effectively curtailed by this method. N-halohydantoins incorporated into irrigation water may be applied directly to plants or to the growth medium in which plants are rooted to treat the plants, to control microorganism development in, on and around the plants and to control certain plant diseases, without harming the plants or interfering with the uptake or utilization of nutrients dissolved in the water.

As noted, it has been found that the relatively low water solubility of N-halohydantoins avoids the formation of a highly concentrated phytotoxic solution. However, the concentration necessary for inhibiting microorganism development is so low that the low solubility of N-halohydantoin does not present a significant obstacle to production of a solution effective in killing microorganisms. Therefore, N-halohydantoin is easily applied and regulated for the appropriate concentration range, and it is essentially unnecessary to provide expensive pumps and other mechanical parts for introduction of N-halohydantoin into a water system, or to introduce the biocide in a meticulously regulated manner to carefully control the N-halohydantoin concentration therein.

N-halohydantoins have been tested and proven compatible with a wide variety of nutrients when added at effective levels directly to the plants watering supply. For example, test additions of effective levels of N-halohydantoins do not inhibit satisfactory uptake of such nutrients as N, P, K, Ca, Mg, B, Cu, Fe, Mn and Zn dissolved in irrigation water.

Preferably, the N-halohydantoin of this invention is an N,N'-dihalohydantoin corresponding to the formula:

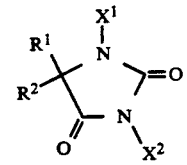

where $R^1$ and $R^2$ are independently selected from among hydrogen and alkyl, and $X^1$ and $X^2$ are independently selected from among fluorine, chlorine, bromine, and iodine. Where $R^1$ and/or $R^2$ are alkyl, they may for example, comprise methyl, ethyl, n-propyl, isopropyl, n-butyl, or n-pentyl. Generally, it is preferred that the constituents comprising $R^1$ and/or $R^2$ contain not more than 5 carbon atoms. Preferred N-halohydantoins are N-halogenated dialkylhydantoins, especially N-halogenated dimethylhydantoins. Particularly preferred N-halohydantoins include 1,3-dibromo-5,5-dimethylhydantoin, 1-bromo-3-chloro-5,5-dimethylhydantoin, and 1,3-dichloro-5,5-dimethylhydantoin, and other hydantoin derivatives.

In this invention, a treatment solution or mixture containing plant nutrients, an N-halohydantoin and water is prepared for application to growing higher order plants to produce healthy plant growth and to inhibit plant diseases and deleterious microorganisms. The order of incorporating the nutrients and N-halohydantoin is not a significant consideration. Either may be added to the water first, or they may be added simultaneously. The concentration of N-halohydantoin in the composition as it is applied to inhibit microorganism development or to control plant disease should be at least about one part per million, and preferably at least about 5 ppm, to be effective against microorganisms and related diseases. However, the concentration of N-halohydantoin in the composition as the composition contacts desired higher order plants should not exceed the point at which the composition becomes phytotoxic or adversely affects the uptake or utilization of the nutrients contained in the water. It has been found that the concentration of N-halohydantoin, due to its low solubility, under ordinary conditions, does not exceed about 1500 ppm, and usually stays in a range below 15 ppm. Except for leaf-tip burn reported on some sensitive plant species at concentrations of 100 ppm or more of N-halohydantoin, phytotoxicity has not been observed at these levels. Additionally, while some impact on nutrient uptake of grain sorghum, a highly iron-sensitive cultivar, was displayed at a concentration of 100 ppm of N-halohydantoin, tests on most plants show no adverse impact on nutrient uptake even at levels many times the recommended concentration of N-halohydantoin for effective use as a biocide. Thus, a biocide of N-halohydantoin concentration between about 1 and about 1500 ppm has been found effective to kill unwanted microorganisms, yet not phytotoxic to higher order plants. The low solubility of N-halohydantoin normally results in concentrations between 2 and 15 ppm, and use of N-halohydantoin at these concentrations is preferred, with concentrations of 5 to 10 ppm of N-halohydantoin most preferred.

The type, manner and concentration of fertilizer to be added to the water system depend on such factors as the type of plants involved, the nature of the water system and the growth medium to be used. The fertilizer can be added to the water supply by use of a standard fertilizer injector or other mechanical means. For example, the fertilizer may first be prepared as a concentrated aqueous solution which is then added to the water supply by use of a proportional injector such as the Dosatron, the Smith injector or the Anderson injector, which have a sensing mechanism for determining the proportion of solution going into the system and which then adjusts the chemical balance so as to obtain the proper dilution.

Principal macronutrients typically added to a nutrient watering supply include nitrogen, phosphorus and potassium. General sources of these nutrients include $Ca(NO_3)_2$, $NaNO_3$, $KNO_3$, Urea, $P_2O_5$, and $K_2O$. Micronutrients, such as Mn, Fe, B, Cu and Zn, are generally present in sufficient quantities in the soil or growth medium without requiring supplemental addition. However, some growth media, such as those based on plastic foams or rock wool, may be deficient in micronutrients, and these may be added by use of many commercially available formulations such as Micro-Max and STEM. Concentrations of macronutrients are generally recommended to be in the range of 100 to 200 ppm for N and K, and 50 to 100 ppm for P, although wider ranges may be permissible. Most micronutrients have much lower recommended concentrations ranging from trace amounts to approximately 35 ppm. For instance, typical concentrations recommended for Mn, Cu, and Mb are 30 ppm, 5 ppm and 6/10 ppm, respectively. Again, a broader range of concentrations may be permissible.

As an example of a typical fertilizer application, Peters Professional Peat-Lite Special 20-10-20 (NPK) fertilizer with micronutrients, a nutrient solution which is widely used by the commercial greenhouse industry, may be added to the nutrient-watering supply. The manufacturer's recommended concentration calls for dissolving 13.5 ounces of the fertilizer per 100 gallons of water capacity. The fertilizer should be reapplied periodically as growth requirements dictate.

The N-halohydantoin may be incorporated into a water system at any point in the system although, of course, for a non-recirculating system the biocidal activity resulting from the N-halohydantoin only occurs downstream of the point of incorporation. Moreover, as noted, due to the largely self-regulatory nature of the N-halohydantoin dissolution at effective concentrations, special pumps and other complex mechanical parts for metering the N-halohydantoin are unnecessary. Satisfactory application can easily be achieved by utilizing a typical fertilizer injector in the manner referred to above for fertilizer applications.

While not a preferred method of application, solid N-halohydantoin, preferably in particulate form, can be placed in a mesh bag and suspended in a stream of water or in a well of a water circulating system. Water contacting the N-halohydantoin in the bag dissolves some of the N-halohydantoin. For a stream the relationship between such factors as water temperature and quality, flow rate and effective area of contact between water and solid biocide should be such that the downstream N-halohydantoin concentration is at least 1 ppm. As noted, due to the relatively low water solubility of N-halohydantoins, the concentration of N-halohydantoin under ordinary conditions automatically remains less than about 10 to 15 ppm. Using a suspended mesh bag containing N-halohydantoin, the concentration readily can be controlled between 2 ppm and 10 ppm. Accordingly, by this essentially passive mechanism, the treated water contains a concentration of N-halohydantoin sufficient to control development of microorganisms and plant disease without impeding nutrient uptake or harming higher order plants.

Preferably, however, N-halohydantoin may be introduced into the water by means of an inexpensive injection devices such as a standard halogenator or brominator. If a brominator is used, either the entire water stream is directed through the brominator, or a side stream is diverted, passed through the brominator and reunited with the main stream. Likewise, for applications of N-halohydantoin by hose, a brominator may be placed in a hose attachment such as those originally intended for application of detergents and cleaning compounds.

For precision application of the N-halohydantoin, the proportional injectors typically used for fertilizers are most preferred. These devices, such as the Dosatron and Smith and Anderson injectors, previously described for fertilizer application, can be operated in substantially the same manner for effective precision application of N-halohydantoin.

There are several uses for the water so treated with N-halohydantoin. For example, the treated water can be applied to an irrigation system to treat the plants and the fruit or seeds they bear, to inhibit the spread of diseases and microorganisms through the irrigation supply system, and, to disinfect the irrigation equipment.

In a greenhouse, plants are often watered by means of a capillary mat irrigation system. In a capillary mat irrigation system, irrigation water typically is delivered through a conduit to a water absorbent sheet of material serving as a sub-irrigation mat. By means of the natural absorbency of the material, the water is transported through the material to the growth medium of potted plants sitting on the absorbent material.

N-halohydantoin may be introduced into a greenhouse irrigation system by directing the stream of water to be used for irrigation through a brominator containing N-halohydantoin. The biocidal activity of the treated water not only tends to prevent development of unwanted microorganisms that otherwise proliferate in the water and on the irrigation equipment, but also prevents the development of microorganisms that otherwise grow and coat the irrigation mat and the pots holding the plants. Thus, by including N-halohydantoin in the system, clogging of the irrigation equipment and coating of the irrigation mat are avoided, and the degradation in efficiency normally encountered over time in this type of irrigation system is suppressed. Application of N-halohydantoin also extends the useful life of the equipment. Further, such treatment of the irrigation water also inhibits development of microorganisms on the floor and other surfaces in the greenhouse often contacted by irrigation water run-off.

As for the plants themselves, the cleaner water provided by this method is believed to deliver to the plants via the roots thereof fewer living microorganisms that could be deleterious to the plant. Moreover, the biocidal activity of the treated water delivered to the plant is believed to inhibit microorganism development in and on the plant, and so helps prevent or control certain plant diseases which could result from pathogenic microorganisms. Importantly, therefore, this method is believed to control diseases that otherwise spread quickly through the plants in a greenhouse. It also prevents spread of disease by recycled greenhouse irrigation water. Yet, despite such biocidal activity of water treated with N-halohydantoin, the plant itself is not harmed by the treated water. Thus, irrigation water can be treated with N-halohydantoin for all these purposes, to treat the irrigated plants, and to avoid fouling and clogging of the irrigation equipment without endangering the plants. Additionally, by incorporating nutrients into the irrigation water supply, healthy plant growth is fostered, with the efficiency and cost-saving advantages of delivering both plant nutrients and biocide in a single system.

As with greenhouse plants, crops or plants in an outdoor nursery may be irrigated with treated water in which both plant nutrients and N-halohydantoin are incorporated. N-halohydantoin may be incorporated anywhere in the water system as described above, and the plants irrigated with the treated water by any of the several irrigation methods, including spray irrigation, trickle or drip irrigation, mist or fog irrigation, sub-irrigation, ebb-and-flow irrigation, and hydroponics. Also as with the greenhouse irrigation methods, the treated water acts to control unwanted microorganisms from developing on the irrigation equipment, as well as in or on the plants and growth medium in which the plants are rooted. The treatment thereby helps prevent certain plant diseases arising from pathogenic microorganisms and controls the outbreak and spread of such diseases.

In an alternative application of the method of the invention, solid N-halohydantoin may be placed on or in the ground near growing plants so that irrigation water containing incorporated nutrients delivers the N-halohydantoin to the plant's roots or rhizosphere. Due to its largely self-regulating quality with regard to concentration attained by dissolution in water, N-halohydantoin applied to growing plants in this manner will be dissolved and delivered to the plants in appropriate dosages.

Thus, N-halohydantoin can be applied in conjunction with irrigation by incorporation into water supplies containing nutrients for watering. Of course, as described in patent application Ser. No. 278,722 filed Dec. 2, 1988 use of N-halohydantoin at the concentrations recommended herein and utilizing the techniques described heretofore, can be used effectively to control plant diseases and microorganisms in, on or around growing, higher order plants without the concurrent addition of plant nutrients.

Other advantages derived from the practice of this invention will become apparent from the following description and examples:

EXAMPLE 1

An experiment was conducted to determine the impact on the uptake and utilization by lettuce, a typical crop, and grain sorghum, a highly Fe-sensitive crop, of nutrients from nutrient watering supplies treated with an N-halohydantoin composition. Peters Professional Peat-Lite Special 20-10-20 fertilizer containing nutrients including N, P, K, Ca, Mg, B, Cu, Fe, Mn and Zn (M-77 Exclusive chelating formula), a nutrient solution widely used in the commercial greenhouse industry, was dissolved in water at the recommended rate of 13.5 oz. per 100 gallons (1.01 g./L.). A solution of 500 ppm 1-bromo-3-chloro-5,5dimethylhydantoin (BCDMH) was dissolved in water to produce treated water supplies of 5 ppm and 100 ppm BCDMH respectively. Five weekly treatments of nutrient-watering solutions containing 0, 5 and 100 ppm BCDMH, respectively, were applied to one series of pots with drain holes each containing 3 lettuce plants rooted in clean quartz, after which the lettuce was harvested. The same treatments were applied to another series of pots with drain holes each containing 6 grain sorghum plants rooted in clean quartz, which also were harvested after treatment. Yields of dry matter and tissue concentrations of N, P, K, Ca, Mg, B, Cu, Fe, Mn and Zn were determined in tops and roots at harvest. Ground tissue samples were analyzed for K, Ca, Mg, Cu, Fe, Mn and Zn with atomic absorption spectroscopy, for P by a vanadate procedure, and for B by the azomethine-H method. N was analyzed using a colorimetric procedure.

The results of the experiment demonstrated no significant adverse impact of BCDMH at the recommended concentration of 5 ppm on either the lettuce or the grain sorghum. Concentrations of BCDMH at greatly in excess of the recommended levels for effective control of microorganisms did show limited impact on lettuce nutrients and exhibited a significant negative effect on the Fe uptake of the highly Fe-sensitive cultivar of grain sorghum. The results of the experiment were as follows:

TABLE 1

Dry matter production and nutrient concentration and uptake by lettuce and grain sorghum, as affected by concentration of BCDMH in the nutrient-watering solution.

| BCDMH conc., ppm | Dry matter, g/plant | Tissue concentration, % | | | | | Tissue concentration, ppm | | | | |
|---|---|---|---|---|---|---|---|---|---|---|---|
| | | N | P | K | Ca | Mg | B | Cu | Fe | Mn | Zn |
| LETTUCE | | | | | | | | | | | |
| Tops | | | | | | | | | | | |
| 0 | 0.44 | 4.43 | 0.63 | 4.08 | 0.32 | 0.11 | 33.6 | 4.9 | 238 | 50 | 28 |
| 5 | 0.54 | 4.11 | 0.62 | 2.85 | 0.41 | 0.16 | 35.9 | 3.8 | 234 | 54 | 29 |
| 100 | 0.39 | 3.80 | 0.50 | 2.76 | 0.32 | 0.14 | 25.2 | 3.6 | 273 | 60 | 32 |
| Roots | | | | | | | | | | | |
| 0 | 0.67 | 1.35 | 0.23 | 6.47 | 0.05 | 0.01 | 19.3 | 4.2 | 965 | 23 | 8 |
| 5 | 0.45 | 1.76 | 0.36 | 10.16 | 0.06 | 0.04 | 19.9 | 5.8 | 1,648 | 29 | 14 |
| 100 | 0.37 | 1.70 | 0.24 | 6.78 | 0.07 | 0.03 | 22.2 | 7.4 | 1,843 | 41 | 21 |
| | | Uptake mg/pot | | | | | Uptake, ug/pot | | | | |
| Tops | | | | | | | | | | | |

TABLE 1-continued

Dry matter production and nutrient concentration and uptake by lettuce and grain sorghum, as affected by concentration of BCDMH in the nutrient-watering solution.

| BCDMH conc., ppm | Dry matter, g/plant | Tissue concentration, % | | | | | Tissue concentration, ppm | | | | |
|---|---|---|---|---|---|---|---|---|---|---|---|
| | | N | P | K | Ca | Mg | B | Cu | Fe | Mn | Zn |
| 0 | 0.44 | 19 | 2.8 | 19 | 1.5 | 0.4 | 16 | 2 | 105 | 25 | 13 |
| 5 | 0.54 | 22 | 3.4 | 21 | 2.2 | 0.9 | 19 | 2 | 127 | 29 | 16 |
| 100 | 0.39 | 14 | 1.9 | 10 | 1.3 | 0.5 | 10 | 2 | 106 | 23 | 12 |
| | | | | | Roots | | | | | | |
| 0 | 0.67 | 9 | 1.4 | 40 | 0.3 | 0.1 | 9 | 3 | 621 | 15 | 5 |
| 5 | 0.45 | 8 | 1.6 | 44 | 0.3 | 0.2 | 10 | 6 | 749 | 13 | 6 |
| 100 | 0.37 | 6 | 0.9 | 26 | 0.2 | 0.1 | 8 | 3 | 693 | 15 | 8 |
| | | | | GRAIN SORGHUM | | | | | | | |
| | | | | | Tops | | | | | | |
| 0 | 1.17 | 3.14 | 0.82 | 3.14 | 0.06 | 0.07 | 11.7 | 5.6 | 85 | 72 | 29 |
| 5 | 0.93 | 3.34 | 0.93 | 3.16 | 0.07 | 0.07 | 11.4 | 6.0 | 78 | 66 | 30 |
| 100 | 0.27 | 2.90 | 0.33 | 1.45 | 0.04 | 0.07 | 12.8 | 5.3 | 133 | 58 | 19 |
| | | | | | Roots | | | | | | |
| 0 | 0.50 | 2.32 | 0.49 | 15.93 | 0.07 | 0.04 | 11.0 | 8.1 | 560 | 54 | 45 |
| 5 | 0.40 | 2.59 | 0.54 | 16.27 | 0.07 | 0.05 | 10.0 | 10.9 | 519 | 47 | 48 |
| 100 | 0.30 | 1.44 | 0.14 | 0.72 | 0.05 | 0.02 | 9.8 | 11.0 | 448 | 6 | 30 |
| | | Uptake, mg/pot | | | | | Uptake, ug/pot | | | | |
| | | | | | Tops | | | | | | |
| 0 | 1.17 | 37 | 9.4 | 37 | 0.7 | 0.8 | 14 | 7 | 93 | 83 | 34 |
| 5 | 0.93 | 30 | 8.3 | 29 | 0.6 | 0.7 | 11 | 5 | 70 | 58 | 26 |
| 100 | 0.27 | 8 | 0.9 | 4 | 0.1 | 0.2 | 3 | 1 | 36 | 16 | 5 |
| | | | | | Roots | | | | | | |
| 0 | 0.50 | 12 | 2.4 | 80 | 0.4 | 0.2 | 5 | 4 | 269 | 27 | 22 |
| 5 | 0.40 | 10 | 2.1 | 63 | 0.3 | 0.2 | 4 | 4 | 245 | 17 | 19 |
| 100 | 0.30 | 5 | 0.4 | 2 | 0.1 | 0.1 | 3 | 3 | 126 | 2 | 9 |

EXAMPLE 2

"Nellie White" Easter lilies, size 8–9 were cultivated using a flooding subirrigation system in which a nutrient solution was recirculated. The nutrient solution contained 100 mg/liter nitrogen and potassium and 40 mg/liter Ca from $KNO_3$, $NH_4NO_3$ and $Ca(NO_3)_2$. The lilies were housed in subirrigation benches 1.2 meters by 3 meters with an independent 200 liter reservoir. As the nutrient solution was pumped onto the benches using Little Giant Model NK-1 metering pumps, the nutrient solution for one set of benches was injected with BCDMH via a Dosatron proportioner/injector at a rate sufficient to provide a concentration of approximately 7 ppm. A control set of benches was similarly irrigated without the addition of BCDMH. Irrigations were spaced out 2 to 4 days apart over a total period of 69 days. Recordings were taken at two week intervals as well as at the conclusion of the experiment as to plant height and dry weight. Also, the number of flower buds per plant and the number of days to flower were determined for the treated and untreated samples. Results of this experiment indicate that BCDMH incorporated within the recommended concentration of 5 to 10 ppm had no significant effect on any of the recorded indications of plant growth. The results are as follows:

TABLE 2

Height, dry matter, buds and days to flow of Easter lillies, as affected by concentration of BCDMH in the nutrient-watering solution.

| | Ht. (cm) | Dry Wt. (g) | # of Days to Buds | # of Days to Flower |
|---|---|---|---|---|
| Nutrients + BCDMH(5–10 ppm) | 40.5 | 18.46 | 5.3 | 83.2 |
| Nutrients − BCDMH(5–10 ppm) | 40.8 | 16.78 | 5.3 | 83.7 |

EXAMPLE 3

Plugs of petunia, tomato, pepper and egg plant were planted one per each 3-in. pot containing growth medium and placed on two benches designed for ebb-and-flow irrigation. Each bench contained 60 pots of each plant arranged in 4 rows of 15 plants each, spaced on 4 in. centers. The plants on the first bench were irrigated with water containing 200 ppm each of N and K and between 10 and 15 ppm BCDMH. The plants on the second (control) bench were irrigated with water containing 200 ppm each of N and K, but without addition of BCDMH. The plants were evaluated after approximately 7 weeks of treatment. At the conclusion, the height above the rim and width of the plants were measured, and plant nutrient levels analyzed. This experiment, using BCDMH at levels above the recommended concentration of 5 to 10 ppm, resulted in no significant differences between the uptake of nutrients by plants treated with BCDMH and those not so treated. The results of the experiment are as follows:

TABLE 3

Height, width and nutrient composition of bedding plants, as affected by concentration of BCDMH in the nutrient-watering solution.

| Plant | Treatment | Height (cm) | Width (cm) | Nutrients (ppm) | | | | |
|---|---|---|---|---|---|---|---|---|
| | | | | N | P | K | Ca | Mg |
| Pepper | Nutrients + BCDMH | 8.4 | 14.9 | 675 | 48+ | 674 | 608 | 217 |
| Pepper | Nutrients − BCDMH | 10.9 | 18.4 | 735 | 48+ | 647 | 585 | 215 |

TABLE 3-continued

Height, width and nutrient composition of bedding plants, as affected by concentration of BCDMH in the nutrient-watering solution.

| Plant | Treatment | Height (cm) | Width (cm) | Nutrients (ppm) | | | | |
|---|---|---|---|---|---|---|---|---|
| | | | | N | P | K | Ca | Mg |
| Tomato | Nutrients + BCDMH | 30.4 | 32.0 | 665 | 48+ | 599 | 505 | 220 |
| Tomato | Nutrients − BCDMH | 29.3 | 33.8 | 675 | 48+ | 599 | 473 | 206 |
| Egg Plant | Nutrients + BCDMH | 7.1 | 10.7 | 530 | 48+ | 466 | 475 | 144 |
| Egg Plant | Nutrients − BCDMH | 7.3 | 11.3 | 460 | 48+ | 464 | 416 | 140 |
| Petunia | Nutrients + BCDMH | 7.8 | 20.5 | 535 | 48+ | 373 | 536 | 199 |
| Petunia | Nutrients − BCDMH | 7.4 | 18.9 | 540 | 48+ | 352 | 389 | 171 |

EXAMPLE 4

Chrysanthemums and gladioli were planted in four 50-foot plots under full-bed culture in EauGallie fine sand. The plants were irrigated by drip irrigation. One week later, BCDMH was introduced into the irrigation water of two of the 50-foot plots. The BCDMH was introduced to the irrigation water by mixing 9% aqueous BCDMH mixture (71 gal.) with water (4000 gal.). The 4071 gallons of total solution were applied to the two 50-foot plots (about 11 acre inches of irrigation) over almost ten weeks. Residual Br- concentration in the water collected from the end of the drip tube during operation was 2 to 2.5 ppm. The following results, showing no adverse effect on either chrysanthemum or gladiolus production, were obtained:

TABLE 4

Growth characteristics as affected by concentration of BCDMH in the nutrient-watering solution.

| | Chrysanthemums: | |
|---|---|---|
| | Weight/Plant (lbs.) | No. of Plants |
| Untreated Plot | 3.6 | 100 |
| Treated Plot | 3.8 | 100 |

| | Gladiolus: | |
|---|---|---|
| | No. of Stems | No. of Florets Per Stem |
| Untreated Plot | 55 | 14.2 |
| Treated Plot | 49 | 14.6 |

No significant difference in microorganism development was apparent between the tubes carrying treated water and those carrying untreated water, but it is believed that the duration of the trial was too short for any significant difference to appear.

EXAMPLE 5

The following plants received a drench of foliar application of a saturated (1500 ppm) BCDMH solution:

| Foliage Crop | Potted Plants |
|---|---|
| Pilea | Grape Ivy |
| Syngonium | Zebra Plant |
| Schefflera | Velvet Plant |
| Pepperomia | English Ivy |
| Dieffenbachia | Christmas Cactus |
| Ficus Benjamina | Asparagus Fern |
| Neanthe Bella | Perrywinkle |
| Maranta Leuconeura | Fibrous Begonia |
| | Coleous |
| | Impatiens |

Applications were intermittent for three to six weeks in a greenhouse environment. No phytotoxicity was observed. In a separate experiment, the same types of plants received foliar sprays containing 1500 ppm BCDMH. Plants received 3 applications of spray separated by 10 day intervals. No phytotoxicity was observed.

The following plants were sprayed with BCDMH solutions of 1, 10, 100 and 1000 ppm in the spring:

| Potted Plants | Flats |
|---|---|
| 8" Zonal Geranium | Fibrous Begonia |
| 3" Tomatoes | Seed Geranium |
| 6" Pot Mums | Non-Stop Begonias |
| 4" Gebera | Petunias |
| | Impatiens |

Except for occasional pinpoint burns on some flowers sprayed with the most concentrated solution, no other signs of phytotoxicity were observed. Undissolved particles of BCDMH are believed to have caused the pinpoint burns. Unopened buds were not harmed.

The following plants in 4-inch pots were sprayed with BCDMH solutions of 1, 10, 100 and 1000 ppm in the summer:

Potted Plants
Pteris Cretica
Gloxinia
African Violet
Gerbera
Non-Stop Begonia

Mild phytotoxicity symptoms were observed on open flowers at 100 and 1000 ppm, but no adverse symptons were observed at 1 or 10 ppm.

EXAMPLE 6

Two sets of Yellow Mandalay chrysanthemums (thirty plants per set) were grown and irrigated by sub-irrigation mats. The plants were fertilized with six ounces of Osmocote per cubic foot of growing medium. One set of plants (control) was not treated with biocide. For the other set of plants (test), BCDMH was injected into the irrigation system at a rate of about 2 to 4 ppm. Bromine levels of the test and control mats were measured daily and the bromine level was maintained 2 to 4 ppm higher than the level of the control. About eleven weeks after planting, leaf samples were collected and analyzed. Table 5 shows levels (in percent by weight) of various nutrients (nutrients for which the fertilizer was the only direct supply) found in the leaves of the two sets of plants:

While the test samples showed lower concentrations of some nutrients, the results suggest that treatment with BCDMH does not significantly affect nutrient uptake. The plants were then evaluated for phytotoxicity. There was no observable phytotoxicity. The plant heights were measured, but no difference was observed between the heights or growth between the treated plants and the control plants.

While considerable algae growth had developed on the mat and fungus gnats had become a problem in the control set, there was no algae growth on the treated mat. Three weeks later, algae growth still had not appeared on the treated mat.

The experiment was repeated with exacum instead of chrysanthemums. Table 6 shows results from the foliar analysis which were obtained:

TABLE 5

| | Chrysanthemums | | | | | | | | | | | |
|---|---|---|---|---|---|---|---|---|---|---|---|---|
| | N | P | K | Ca | Mg | Mn | Fe | B | Cu | Zn | Al | Na |
| Control | 3.42 | 0.23 | 4.1 | 2.2 | 0.64 | 339 | 111 | 20 | 7.7 | 181 | 34 | 25 |
| Test | 3.32 | 0.12 | 1.6 | 1.0 | 0.39 | 208 | 54 | 11 | 4.6 | 126 | 22 | 21 |

TABLE 6

| | Exacums | | | | | | | | | | | |
|---|---|---|---|---|---|---|---|---|---|---|---|---|
| | N | P | K | Ca | Mg | Mn | Fe | B | Cu | Zn | Al | Na |
| Control | 4.32 | 0.30 | 1.21 | 0.75 | 0.69 | 229 | 87.9 | 39 | 4.7 | 49.7 | 20.9 | 8626 |
| Test | 4.24 | 0.37 | 0.89 | 0.83 | 0.80 | 222 | 92.7 | 47.6 | 5.1 | 70.6 | 23.1 | 9376 |

The results of this test also indicate that treatment with BCDMH at the levels utilized does not significantly affect nutrient uptake.

In view of the above, it will be seen that the several objects of the invention are achieved and other advantageous results attained.

What is claimed is:

1. A method for controlling plant diseases and unwanted microorganisms by incorporating N-halohydantoins in nutrient-watering solution, the method comprising:
   preparing a treatment mixture comprising plant nutrients, an N-halohydantoin and water; and
   contacting a plant rooted in a solid growth medium with said mixture, thereby inhibiting the growth of disease or unwanted microorganisms on, in or around said plant, said mixture being viable for use in stimulating healthy plant growth.

2. A method as set forth in claim 1 wherein the N-halohydantoin comprises an N-halogenated dialkylhydantoin.

3. A method as set forth in claim 2 wherein the N-halohydantoin comprises an N-halogenated dimethylhydantoin.

4. A method as set forth in claim 3 wherein the N-halohydantoin is selected from the group consisting of bromo-chloro-dimethylhydantoin, dibromo-dimethylhydantoin and dichloro-dimethylhydantoin.

5. A method as set forth in claim 4 wherein the N-halohydantoin comprises bromo-chloro-dimethylhydantoin.

6. A method for irrigating growing plants rooted in a solid growth medium wherein needed nutrients are supplied to the plants and disease or growth of unwanted microorganisms on or in the plants is inhibited without harming the growth of the plants, the method comprising:
   preparing treated water containing plant nutrients and an N-halohydantoin; and
   continuously or recurrently irrigating plants rooted in a solid growth medium with said treated water.

7. A method as set forth in claim 6 wherein the plants are irrigated by means of spray irrigation.

8. A method as set forth in claim 6 wherein irrigation of the plant comprises transporting the treated water to the plants via a water absorbent material that is in contact with said plant or said growth medium in which it is rooted.

9. A method as set forth in claim 6 wherein the N-halohydantoin comprises an N-halogenated dialkylhydantoin.

10. A method as set forth in claim 9 wherein the N-halohydantoin comprises an N-halogenated dimethylhydantoin.

11. A method as set forth in claim 10 wherein the N-halohydantoin is selected from the group consisting of bromo-chloro-dimethylhydantoin, dibromo-dimethylhydantoin and dichloro-dimethylhydantoin.

12. A method as set forth in claim 11 wherein the N-halohydantoin comprises bromo-chloro-dimethylhydantoin.

13. A method for irrigating growing plants rooted in a solid growth medium wherein the plants are irrigated by transportation of water to the plants by a water-absorbent material wherein disease or growth of unwanted microorganisms on or in the plants are controlled without harming the growth of the plants and needed nutrients are supplied to the plants, the method comprising:
   arranging the plants and the water-absorbent material so that water may be transported through the water-absorbent material and contact the plants or said growth medium in which they are rooted;
   preparing treated water containing plant nutrients and an N-halohydantoin; and
   continuously or recurrently delivering said treated water to said water-absorbent material, thereby effecting transport of treated water to said plants or said growth medium.

14. A method as set forth in claim 13 wherein the concentration of N-halohydantoin is between about 1 ppm and about 1500 ppm by weight.

15. A method as set forth in claim 19 wherein the N-halohydantoin comprises an N-halogenated dimethylhydantoin.

16. A method as set forth in claim 15 wherein the N-halohydantoin is selected from the group consisting of bromo-chloro-dimethylhydantoin, dibromo-dimethylhydantoin and dichloro-dimethylhydantoin.

17. A method as set forth in claim 16 wherein the N-halohydantoin comprises bromo-chloro-dimethylhydantoin.

18. A method for controlling disease or growth of unwanted microorganisms in a growing plant or its rhizosphere without harming the plant, the method comprising applying an N-halohydantoin to a growth medium in which the plant is rooted, the N-halohydantoin being continuously or recurrently dissolved in and conveyed to said rhizosphere by irrigation water received by said growth medium, said irrigation water further containing plant nutrients.

19. A method as set forth in claim 18 wherein the N-halohydantoin comprises an N-halogenated dialkylhydantoin.

20. A method as set forth in claim 19 wherein the N-halohydantoin comprises an N-halogenated dimethylhydantoin.

21. A method as set forth in claim 20 wherein the N-halohydantoin is selected from the group consisting of bromo-chloro-dimethylhydantoin, dibromo-dimethylhydantoin and dichloro-dimethylhydantoin.

22. A method as set forth in claim 21 wherein the N-halohydantoin comprises bromo-chloro-dimethylhydantoin.

* * * * *